United States Patent
Burnes et al.

(10) Patent No.: US 12,369,834 B2
(45) Date of Patent: *Jul. 29, 2025

(54) TRIGGERING STORAGE OF ELECTROCARDIOGRAPHS FOR DETECTED PREMATURE VENTRICULAR CONTRACTIONS (PVCs)

(71) Applicant: Medtronic, Inc., Minneapolis, MN (US)

(72) Inventors: John E. Burnes, Blaine, MN (US); Shantanu Sarkar, Roseville, MN (US); Gautham Rajagopal, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/348,040

(22) Filed: Jul. 6, 2023

(65) Prior Publication Data

US 2023/0346287 A1 Nov. 2, 2023

Related U.S. Application Data

(63) Continuation of application No. 16/921,346, filed on Jul. 6, 2020, now Pat. No. 11,717,208.

(Continued)

(51) Int. Cl.
*A61B 5/00* (2006.01)
*A61B 5/316* (2021.01)
(Continued)

(52) U.S. Cl.
CPC .............. *A61B 5/333* (2021.01); *A61B 5/316* (2021.01); *A61B 5/339* (2021.01); *A61B 5/349* (2021.01); *A61B 5/352* (2021.01); *G16H 50/70* (2018.01)

(58) Field of Classification Search
CPC ......... A61B 5/333; A61B 5/316; A61B 5/339; A61B 5/352; A61B 5/349–366; G16H 50/70

See application file for complete search history.

(56) References Cited

U.S. PATENT DOCUMENTS

| | | |
|---|---|---|
| 4,531,527 A | 7/1985 | Reinhold, Jr. et al. |
| 4,552,154 A | 11/1985 | Hartlaub |

(Continued)

FOREIGN PATENT DOCUMENTS

| | | |
|---|---|---|
| CN | 202027572 U | 11/2011 |
| CN | 107529998 A | 1/2018 |

(Continued)

OTHER PUBLICATIONS

Alqarawi et al., "Identifying and Managing Premature Ventricular Contraction-Induced Cardiomyopathy: What, Why, and How?," Canadian Journal of Cardiology, vol. 33, Feb. 2017, pp. 287-290.

(Continued)

*Primary Examiner* — Scott M. Getzow
(74) *Attorney, Agent, or Firm* — Shumaker & Sieffert, P.A.

(57) ABSTRACT

Techniques for triggering the storage or transmission of cardiac electrogram (EGM) signals associated with a premature ventricular contractions (PVC) include sensing a cardiac EGM signal of a patient via a plurality of electrodes, detecting a premature ventricular contraction (PVC) within the cardiac EGM signal, determining whether PVC storage criteria is met, in response to a determination that the PVC storage criteria is met, storing a portion of the cardiac EGM signal associated with the PVC, and in response to a determination that the PVC storage criteria is not met, eschewing storing the portion of the cardiac EGM signal associated with the PVC.

20 Claims, 11 Drawing Sheets

Related U.S. Application Data

(60) Provisional application No. 62/927,932, filed on Oct. 30, 2019.

(51) Int. Cl.

| | |
|---|---|
| A61B 5/333 | (2021.01) |
| A61B 5/339 | (2021.01) |
| A61B 5/349 | (2021.01) |
| A61B 5/352 | (2021.01) |
| G16H 50/70 | (2018.01) |

(56) References Cited

U.S. PATENT DOCUMENTS

| | | | |
|---|---|---|---|
| 5,159,932 | A | 11/1992 | Zanetti et al. |
| 6,453,192 | B1 | 9/2002 | Ding et al. |
| 6,954,671 | B1 | 10/2005 | Hoijer et al. |
| 7,027,858 | B2 | 4/2006 | Cao et al. |
| 7,751,876 | B2 | 7/2010 | Healey |
| 7,778,699 | B1 | 8/2010 | Ferrise et al. |
| 8,027,722 | B1 | 9/2011 | Nabutovsky |
| 8,380,294 | B2 | 2/2013 | Messier et al. |
| 8,457,728 | B2 | 6/2013 | Schneider et al. |
| 8,704,688 | B2 | 4/2014 | Shen et al. |
| 8,855,755 | B2 | 10/2014 | Zhang et al. |
| 8,989,852 | B2 | 3/2015 | Gill et al. |
| 9,427,594 | B1 | 8/2016 | Bornzin et al. |
| 9,492,138 | B2 | 11/2016 | Kapoor |
| 9,675,270 | B2 | 6/2017 | Sarkar |
| 9,706,938 | B2 | 7/2017 | Chakravarthy et al. |
| 9,936,890 | B2 | 4/2018 | Sarkar |
| 9,968,274 | B2 | 5/2018 | Korzinov et al. |
| 10,779,744 | B2 | 9/2020 | Rapin et al. |
| 11,234,629 | B2 | 2/2022 | Liu et al. |
| 2007/0255345 | A1 | 11/2007 | Krause |
| 2009/0299422 | A1 | 12/2009 | Ousdigian et al. |
| 2010/0274148 | A1 | 10/2010 | Zhang et al. |
| 2012/0277608 | A1 | 11/2012 | Schneider et al. |
| 2014/0107723 | A1 | 4/2014 | Hou et al. |
| 2014/0276928 | A1 | 9/2014 | Vanderpool et al. |
| 2015/0335894 | A1 | 11/2015 | Bornzin et al. |
| 2016/0135706 | A1 | 5/2016 | Sullivan et al. |
| 2016/0310029 | A1 | 10/2016 | Sarkar |
| 2016/0310031 | A1 | 10/2016 | Sarkar |
| 2017/0119274 | A1 | 5/2017 | Chakravarthy et al. |
| 2018/0303345 | A1 | 10/2018 | Adler |
| 2019/0051393 | A1 | 2/2019 | Whiting et al. |
| 2019/0216350 | A1 | 7/2019 | Sullivan et al. |
| 2019/0336032 | A1 | 11/2019 | Gill et al. |
| 2020/0237314 | A1 | 7/2020 | Qu et al. |
| 2020/0357519 | A1 | 11/2020 | Chakravarthy et al. |
| 2020/0383597 | A1 | 12/2020 | Rajagopal et al. |
| 2021/0128005 | A1 | 5/2021 | Burnes et al. |

FOREIGN PATENT DOCUMENTS

| | | |
|---|---|---|
| CN | 108024717 A | 5/2018 |
| WO | 2004096353 A1 | 11/2004 |

OTHER PUBLICATIONS

Callans, "Premature Ventricular Contraction-induced Cardiomyopathy," Arrhythmia & Electrophysiology Review, vol. 6, Dec. 2017, pp. 153-155.

Cho et al., "PVC Classification Algorithm Through Efficient R Wave Detection," Journal of Sensor Science and Technology, vol. 22, No. 5, Sep. 30, 2013, pp. 338-345.

International Search Report and Written Opinion of International Application No. PCT/US2020/054895, mailed Jan. 21, 2021, 11 pp.

Kaya et al., "Classification of Premature Ventricular Contraction in ECG", International Journal of Advanced Computer Science and Applications, vol. 6, No. 7, 2015, pp. 34-40, Retrieved from the Internet on Jan. 31, 2023 from URL: https://avesis.ktu.edu.tr/yayin/9437012c-c146-4e8a-a482-1cc8653890a6/classification-of-premature-ventricular-contraction-in-ecg.

Mazidi et al., "Detection of premature ventricular contraction (PVC) using linear and nonlinear techniques: an experimental study", Cluster Computing, vol. 23, No. 2, Springer Science+Business Media, LLC, Jul. 11, 2019, pp. 759-774, URL: https://link.springer.com/article/10.1007/s10586-019-02953-x.

Panela et al., "Ablation of frequent PVC in patients meeting criteria for primary prevention ICD implant: Safety of withholding the implant," Heart Rhythm Society, vol. 12, No. 12, Dec. 2015, pp. 2434-2442.

Panela et al., "Clinical recognition of pure premature ventricular complex-induced cardiomyopathy at presentation," Heart Rhythm Society, vol. 14, No. 12, Dec. 2017, pp. 1864-1870.

Panela et al., "Neurohormonal, Structural, and Functional Recovery Pattern After Premature Ventricular Complex Ablation is Independent of Structural Heart Disease Status in Patients with Depressed Left Ventricular Ejection Fraction: A Prospective Multicenter Study," Journal of the American College of Cardiology, vol. 62, No. 13, Sep. 24, 2013, pp. 1195-1202.

Prosecution History from U.S. Appl. No. 16/436,012, dated Dec. 1, 2020 through Mar. 30, 2023, 226 pp.

Prosecution History from U.S. Appl. No. 16/921,346, dated Dec. 30, 2021 through Mar. 30, 2023, 93 pp.

Rodrigues De Oliveira et al., , "Geometrical Features for Premature Ventricular Contraction Recognition with Analytic Hierarchy Process Based Machine Learning Algorithms Selection," Computer Methods and Programs in Biomedicine, vol. 169, Feb. 1, 2019, pp. 59-69.

Talbi, M.L. et al., "PVC discrimination using the QRS power spectrum and self-organizing maps," Computer Methods and Programs in Biomedicine, Elsevier, Masterdam, NL, vol. 94, No. 3, Jun. 1, 2009, pp. 223-231.

U.S. Appl. No. 18/050,814, filed Oct. 28, 2022, naming inventors Rajagopal et al.

Zhang et al., "Premature Ventricular Contractions' Detection Based on Active Learning", Scientific Programming, vol. 2021, Mar. 8, 2021, 14 pp., URL: https://www.hindawi.com/journals/sp/2021/5556011/.

Zhou, "Automatic Detection of Premature Ventricular Contraction Using Quantum Neural Networks", Automatic detection of premature Third IEEE Symposium on Bioinformatics and Bioengineering, IEEE, Mar. 12, 2003, pp. 169-173, URL: https://citeseerx.ist.psu.edu/viewdoc/download?doi=10.1.1.138.1032&rep=rep1&type=pdf.

Office Action from U.S. Appl. No. 18/621,766 dated Jul. 10, 2024, 10 pp.

U.S. Appl. No. 18/621,766, filed Mar. 29, 2024, by Burnes et al.

Appeal Brief from U.S. Appl. No. 16/436,012, filed Jul. 27, 2023, 121 pp.

Examiner's Answer from U.S. Appl. No. 16/436,012 dated Oct. 2, 2023, 16 pp.

Notice of Allowance from U.S. Appl. No. 18/621,766 dated Oct. 10, 2024, 5 pp.

Response to Office Action dated Jul. 10, 2024 from U.S. Appl. No. 18/621,766, filed Sep. 23, 2024, 21 pp.

Office Action from counterpart Chinese Application No. 202080075130.5 dated Feb. 18, 2025, 15 pp. Translation Attached.

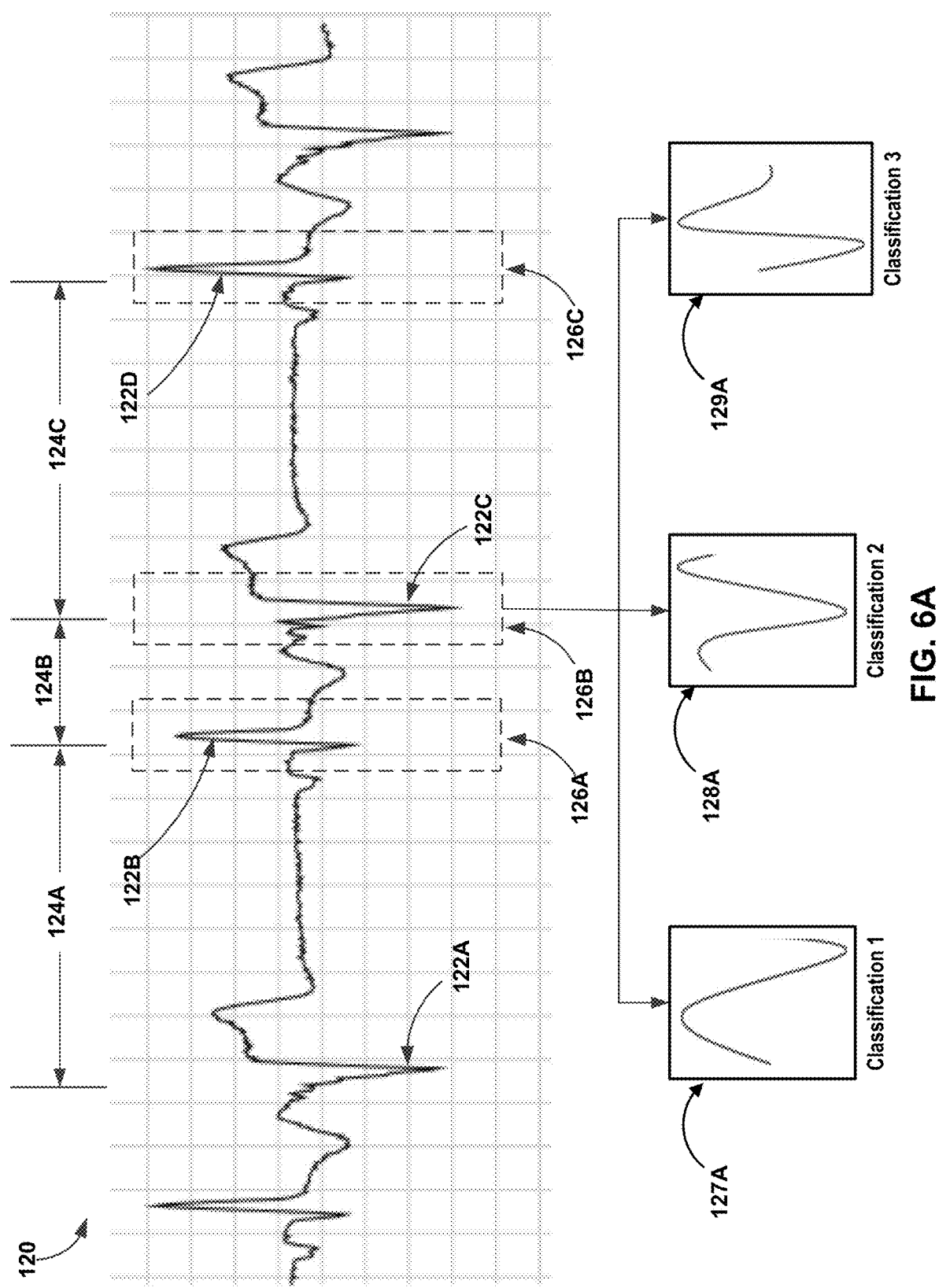

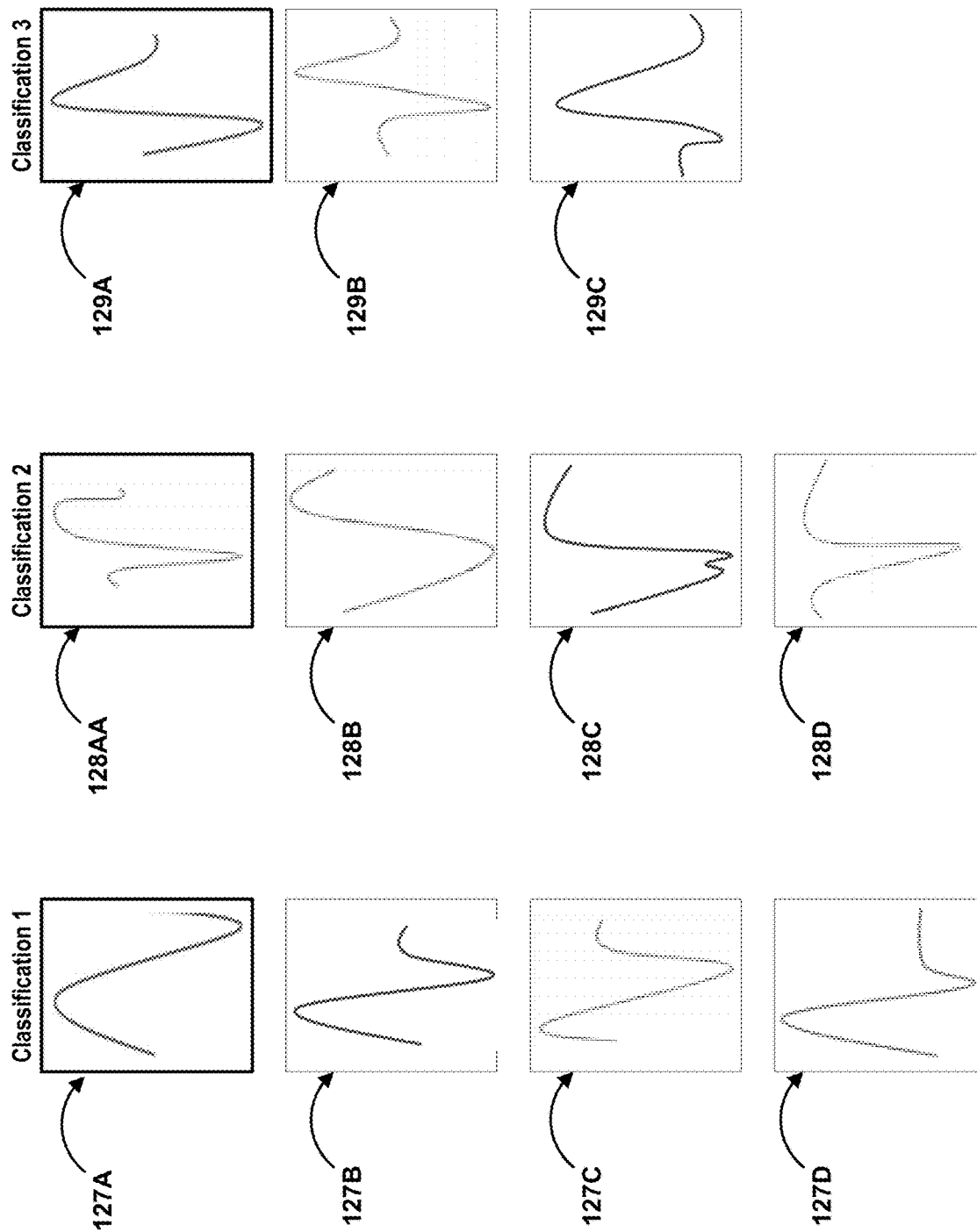

TRIGGERING STORAGE OF ELECTROCARDIOGRAPHS FOR DETECTED PREMATURE VENTRICULAR CONTRACTIONS (PVCs)

This application is a continuation of U.S. patent application Ser. No. 16/921,346, filed on Jul. 6, 2020, which claims the benefit of U.S. Provisional Patent Application No. 62/927,932, filed on Oct. 30, 2019, the entire content of which is incorporated herein by reference.

FIELD

The disclosure relates generally to medical device systems and, more particularly, medical device systems configured to detect premature ventricular contractions (PVCs).

BACKGROUND

Medical devices may be used to monitor physiological signals of a patient. For example, some medical devices are configured to sense cardiac electrogram (EGM) signals indicative of the electrical activity of the heart via electrodes. Some medical devices may be configured to deliver a therapy in conjunction with or separate from the monitoring of physiological signals.

PVCs are premature heartbeats. PVCs are premature because they occur before the regular heartbeat. During a PVC event, the ventricles electrically discharge and contract prematurely before the normal electrical discharge arrives from the sinoatrial node. PVCs may occur in healthy individuals. PVCs may be caused by caffeine, smoking, alcohol consumption, stress, exhaustion, pharmacological toxicity, electrolyte imbalance, lack of oxygen, and heart attack as examples. Common symptoms associated with PVCs include palpitations, dizziness, fatigue, dyspnea, chest pain, and lightheadedness. PVCs are normally considered benign, but may potentially cause cardiomyopathy, ventricular arrythmias, and heart failure.

Management strategies for PVC induced cardiomyopathy include medical therapy and catheter ablation, with an increasing role for catheter ablation in view of the potential for permanent suppression of PVCs. Ablation to suppress PVCs may lead to improvement of left ventricular systolic dysfunction (LVSD) and normalization of left ventricular ejection fraction (LVEF). PVC burden, i.e., a quantification of the amount of PVCs over a period of time, can be an independent predictor of PVC induced cardiomyopathy. Presently, 24-hour Holter monitoring is the most commonly used method to determine PVC burden.

SUMMARY

In general, this disclosure is directed to techniques for detecting PVCs using a medical device. More particularly, the disclosure is directed to techniques for triggering the storage or transmission of cardiac EGM signals associated with a PVC in response to one or more PVC storage criteria being met. For example, processing circuitry of an implantable medical device (IMD) or another device may identify a PVC in a cardiac EGM signal, classify the PVC, and store or transmit the PVC signal to a server or remote computing device when a PVC burden is above a PVC burden threshold or when a new PVC classification is detected. In this way, the processing circuitry may only store or transmit the cardiac EGM signals necessary to aid a physician while conserving storage space and battery life of the device by not storing or transmitting every single detected PVC. Moreover, storing or transmitting PVCs in response to the PVC burden for a given patient exceeding the PVC burden threshold may help determine that the patient is experiencing one or more patient conditions such as such as risk of sudden cardiac death, arrhythmias, or cardiomyopathy.

EGM signals, in some cases, may indicate one or more events of a heart cycle such as ventricular depolarizations and/or repolarizations, atrial depolarizations and/or repolarizations, or any combination thereof. Such EGMs may be referred to as cardiac EGMs or cardiac EGM signals. PVCs can be detected in cardiac EGM signals. While PVCs are common and usually harmless, they can be dangerous for persons with existing heart problems. Therefore, it may be helpful for physicians to detect and identify patterns of PVCs to better treat their patients, particularly patients with existing heart problems. For example, physicians may want to view and analyze EGM data about the morphologies of the PVCs detected in a particular patient. This data can include exemplary PVC morphologies, classes of PVC morphologies, or morphologies of PVCs occurring within a period of time (e.g., a day, a week, a month) or in particular intervals of time (e.g., hourly, daily, weekly). By providing exemplary morphologies or classes of PVC morphologies detected in a patient to a physician, a system in accordance with this disclosure may assist a physician to localize the origin of the PVCs and/or determine whether there are multiple triggers causing the PVCs. This may facilitate more accurate determinations of cardiac wellness and risk of sudden cardiac death, and may lead to clinical interventions to suppress PVCs such as medications and PVC ablations of targeted areas of the heart.

In one example, a medical system comprises a plurality of electrodes configured to sense a cardiac electrogram (EGM) signal of a patient; and processing circuitry configured to detect a premature ventricular contraction (PVC) within the cardiac EGM signal; determine whether PVC storage criteria is met; in response to a determination that the PVC storage criteria is met, store a portion of the cardiac EGM signal associated with the PVC; and in response to a determination that the PVC storage criteria is not met, eschew storing the portion of the cardiac EGM signal associated with the PVC.

In another example, a method comprises sensing a cardiac electrogram (EGM) signal of a patient via a plurality of electrodes; detecting a premature ventricular contraction (PVC) within the cardiac EGM signal; determining whether PVC storage criteria is met; in response to a determination that the PVC storage criteria is met, storing a portion of the cardiac EGM signal associated with the PVC; and in response to a determination that the PVC storage criteria is not met, eschewing storing the portion of the cardiac EGM signal associated with the PVC.

In another example, a non-transitory computer-readable medium comprising instructions for causing one or more processors to sense a cardiac electrogram (EGM) signal of a patient; detect a premature ventricular contraction (PVC) within the cardiac EGM signal; determine whether PVC storage criteria is met; in response to a determination that the PVC storage criteria is met, store a portion of the cardiac EGM signal associated with the PVC; and in response to a determination that the PVC storage criteria is not met, eschew storing the portion of the cardiac EGM signal associated with the PVC.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

FIG. 6A is a graph illustrating a cardiac EGM signal and an example technique for detecting and classifying PVCs based on cardiac EGM signal.

FIG. 6B illustrates exemplary classified PVC cardiac EGM signals.

Like reference characters denote like elements throughout the description and figures.

DETAILED DESCRIPTION

Figure 1:
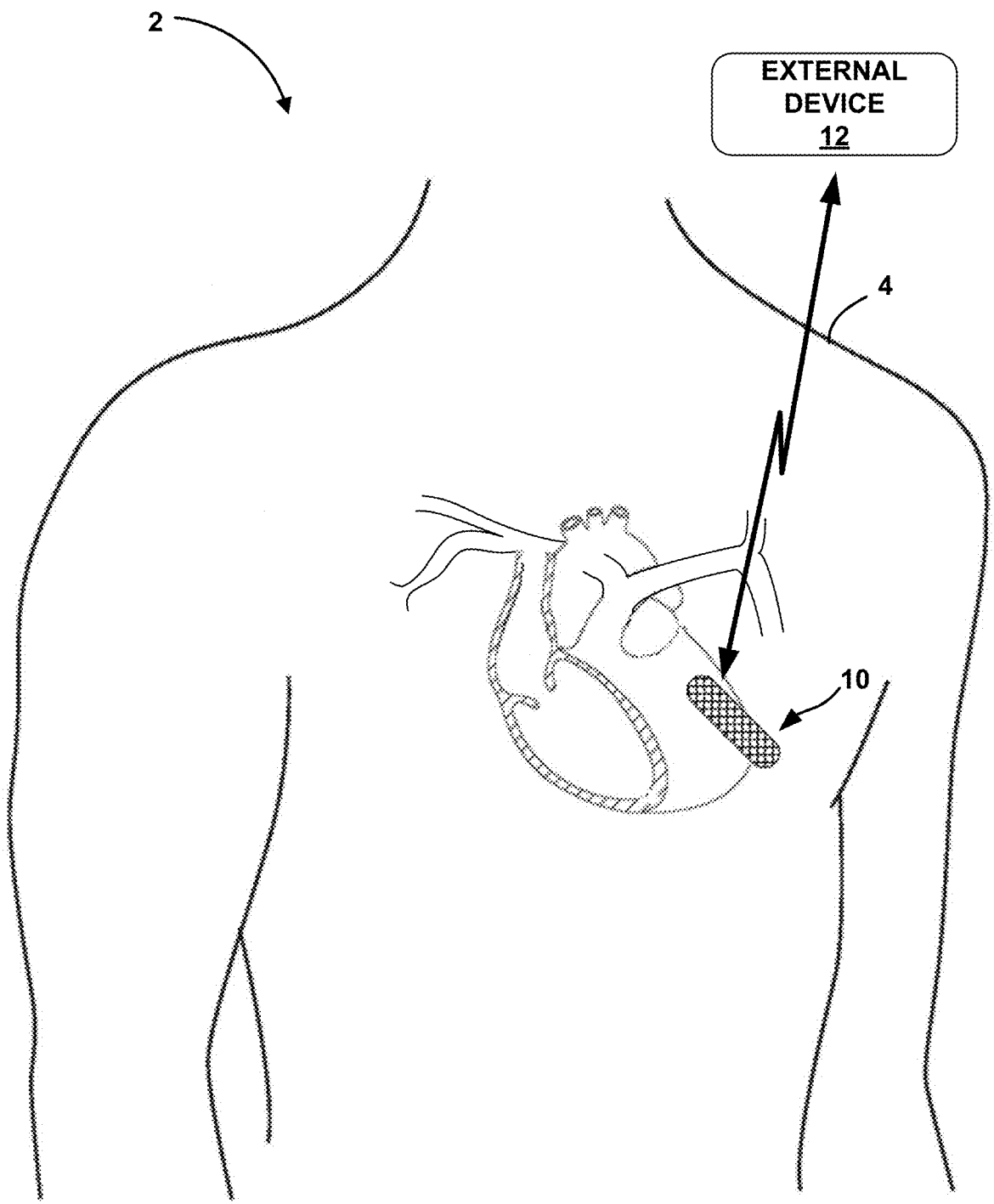
FIG. 1 illustrates the environment of an example medical system in conjunction with a patient.

A variety of types of medical devices sense cardiac EGMs. Some medical devices that sense cardiac EGMs are non-invasive, e.g., using a plurality of electrodes placed in contact with external portions of the patient, such as at various locations on the skin of the patient. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Some implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Any medical device configured to sense a cardiac EGM via implanted or external electrodes, including the examples identified herein, may implement the techniques of this disclosure for detecting a PVC in a cardiac EGM, classifying the PVC, and storing a portion of the cardiac EGM signal associated with PVC when one or more PVC storage criteria is met. The techniques of this disclosure for triggering storage of cardiac EGM signals associated with a PVC may facilitate determinations of cardiac wellness and risk of sudden cardiac death, and may lead to clinical interventions to suppress PVCs such as medications and PVC ablations.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. IMD 10 may transmit data to external device 12 (or any other device). The transmitted data may include values of physiological parameters measured by IMD 10, indications of episodes of arrhythmia or other maladies detected by IMD 10, and physiological signals recorded by IMD 10. For example, external device 12 may receive information related to detection of PVCs by IMD 10, such as at least a portion of a cardiac EGM signal, morphological information about PVCs or a count or other quantification of PVCs, e.g., over a time period. In some examples, IMD 10 may transmit cardiac EGM segments due to IMD 10 determining that an episode of arrhythmia or another malady occurred during the segment, or in response to a request to record the segment from patient 4 or another user. In some examples, IMD 10 takes the form of the LINQ™ ICM, or another ICM similar to, e.g., a version or modification of, the LINQ™ ICM.

External device 12 may be a computing device with a display viewable by the user and an interface for providing input to external device 12 (i.e., a user input mechanism). In some examples, external device 12 may be a notebook computer, tablet computer, workstation, one or more servers, cloud, data center, cellular phone, personal digital assistant, or another computing device that may run an application that enables the computing device to interact with IMD 10. External device 12 is configured to communicate with 1 MB 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

External device 12 may be used to configure operational parameters for IMD 10. External device 12 may be used to retrieve data from 1 MB 10. The retrieved data may include values of physiological parameters measured by IMD 10, indications of episodes of arrhythmia or other maladies detected by IMD 10, and physiological signals recorded by IMD 10. For example, external device 12 may retrieve information related to detection of PVCs by IMD 10, such as at least a portion of a cardiac EGM signal, morphological information about PVCs or a count or other quantification of PVCs, e.g., over a time period since the last retrieval of information by external device. External device 12 may also retrieve cardiac EGM segments recorded by IMD 10, e.g., due to IMD 10 determining that an episode of arrhythmia or another malady occurred during the segment, or in response to a request to record the segment from patient 4 or another user. As discussed in greater detail below with respect to FIG. 5, one or more remote computing devices may interact with IMD 10 in a manner similar to external device 12, e.g., to program IMD 10 and/or exchange data with IMD 10, via a network.

Processing circuitry of medical system 2, e.g., of IMD 10, external device 12, and/or of one or more other computing devices, may be configured to perform the example techniques of this disclosure for detecting a PVC, classifying the PVC, and, in response to one or more PVC storage criteria being met, triggering the storage or transmission of cardiac EGM information associated with the PVC. In some examples, the processing circuitry of medical system 2 analyzes a cardiac EGM signals sensed by IMD 10 to determine whether a PVC has occurred. The PVC storage criteria may include a PVC burden being above a PVC burden threshold or when a new PVC classification is detected, as described in greater detail below. Although described in the context of examples in which IMD 10 that senses the cardiac EGM comprises an insertable cardiac monitor, example systems including one or more implantable or external devices of any type configured to sense a cardiac EGM may be configured to implement the techniques of this disclosure.

Figure 2:
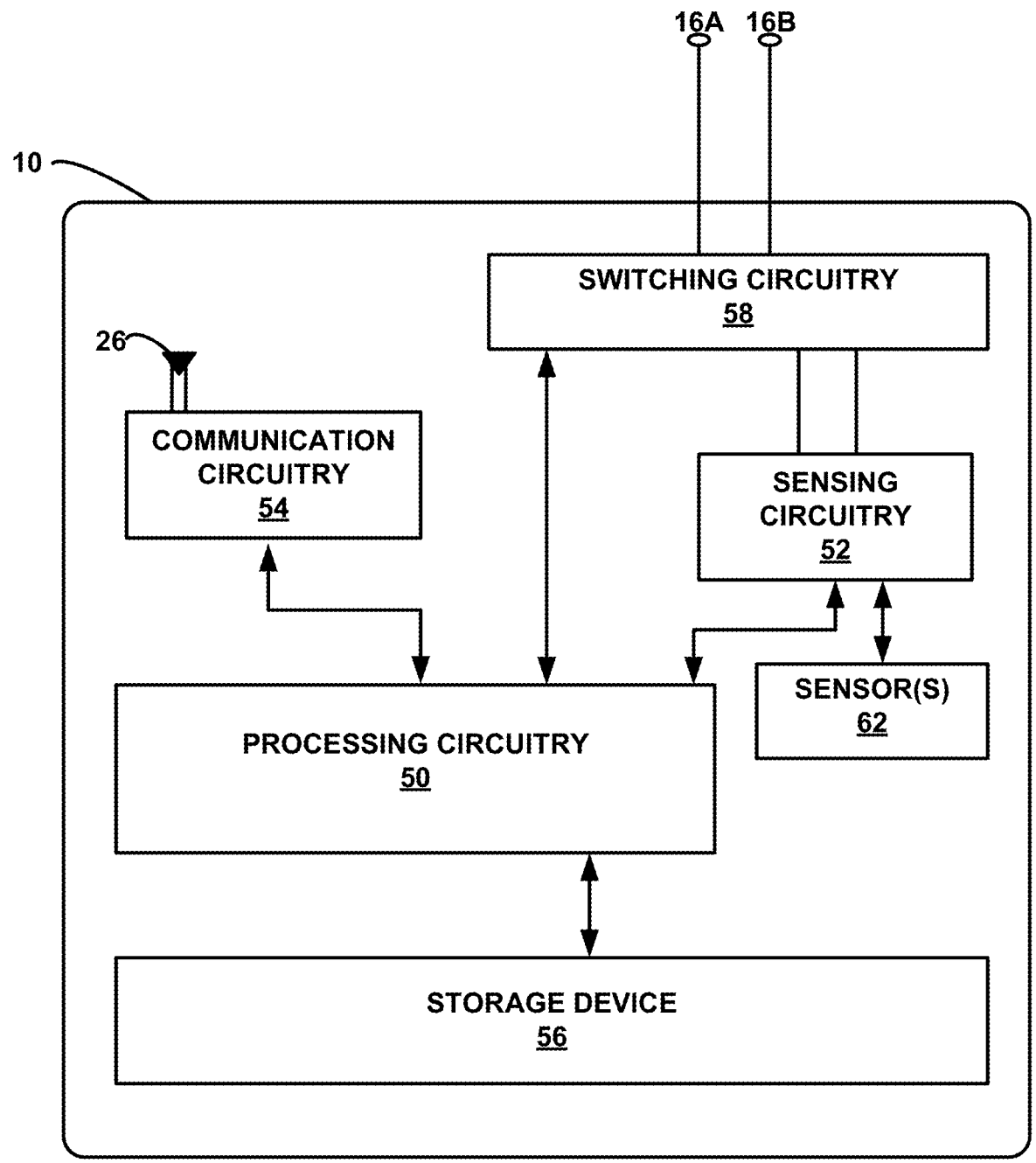
FIG. 2 is a functional block diagram illustrating an example configuration of the implantable medical device (IMD) of the medical system of FIG. 1.

FIG. 2 is a functional block diagram illustrating an example configuration of IMD 10 of FIG. 1 in accordance with one or more techniques described herein. In the illustrated example, IMD 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

Sensing circuitry 52 and/or processing circuitry 50 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 52 may include a rectifier, filter, amplifier, comparator, and/or analog-to-digital converter, in some examples. In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining inter-depolarization intervals, heart rate, and detecting arrhythmias, such as tachyarrhythmias and asystole.

Sensing circuitry 52 may also provide one or more digitized cardiac EGM signals to processing circuitry 50 for analysis, e.g., for use in detecting a PVC, and/or for analysis to determine whether one or more PVC storage criteria are satisfied according to the techniques of this disclosure. In some examples, processing circuitry 50 may store the digitized cardiac EGM or one or more portions of the digitized cardiac EGM associated with a PVC in storage device 56. Processing circuitry 50 of IMD 10, and/or processing circuitry of another device that retrieves or receives data from IMD 10, may analyze the cardiac EGM to determine whether one or more PVC storage criteria are satisfied according to the techniques of this disclosure.

Communication circuitry 54 may include any suitable hardware, firmware, software or any combination thereof for communicating with another device, such as external device 12, another networked computing device or server, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth, Wi-Fi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include at least a portion of a cardiac EGM signal associated with one or more PVCs, morphological information about PVCs, a count or other quantification of PVCs, and/or other cardiac EGM information, as examples.

Figure 3:
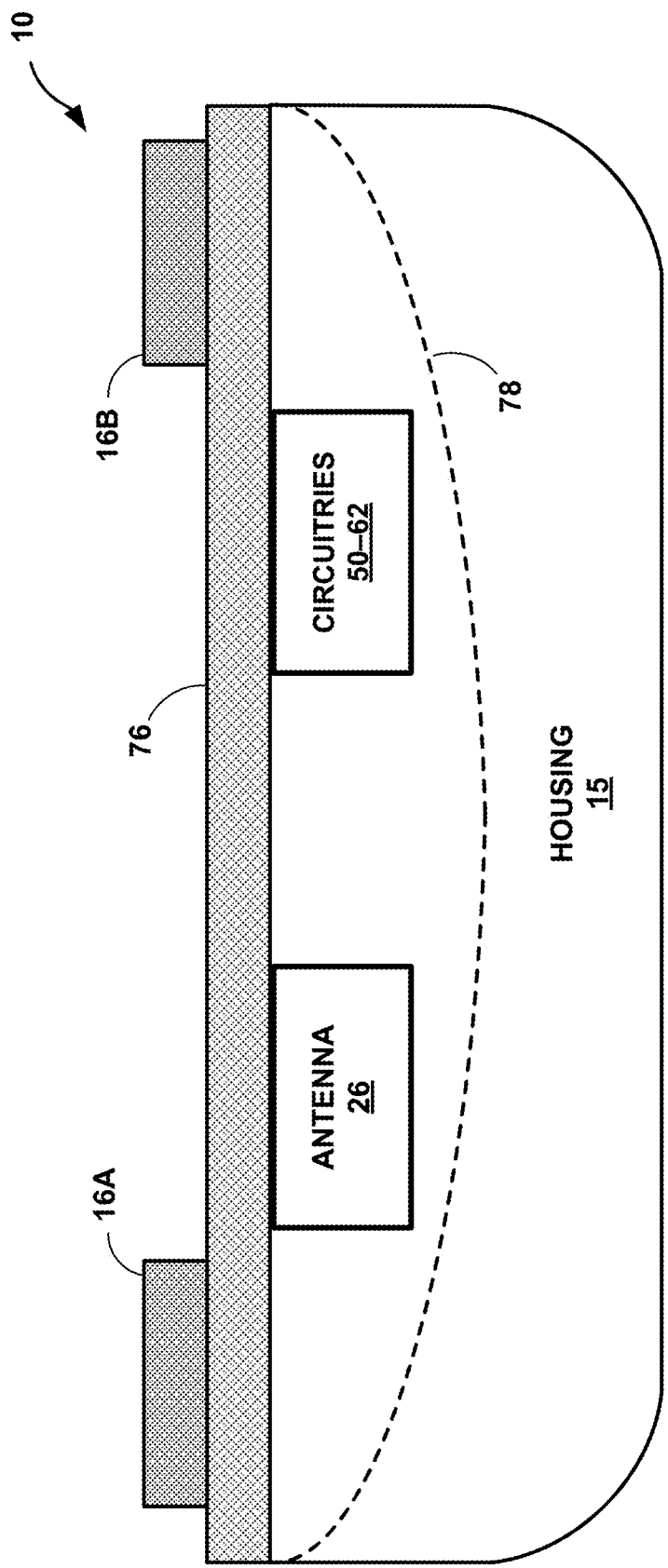
FIG. 3 is a conceptual side-view diagram illustrating an example configuration of the IMD of FIGS. 1 and 2.

FIG. 3 is a conceptual side-view diagram illustrating an example configuration of IMD 10 of FIGS. 1 and 2. In the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, one or more of sensors 62 may be formed or placed on the outer surface of cover 76. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
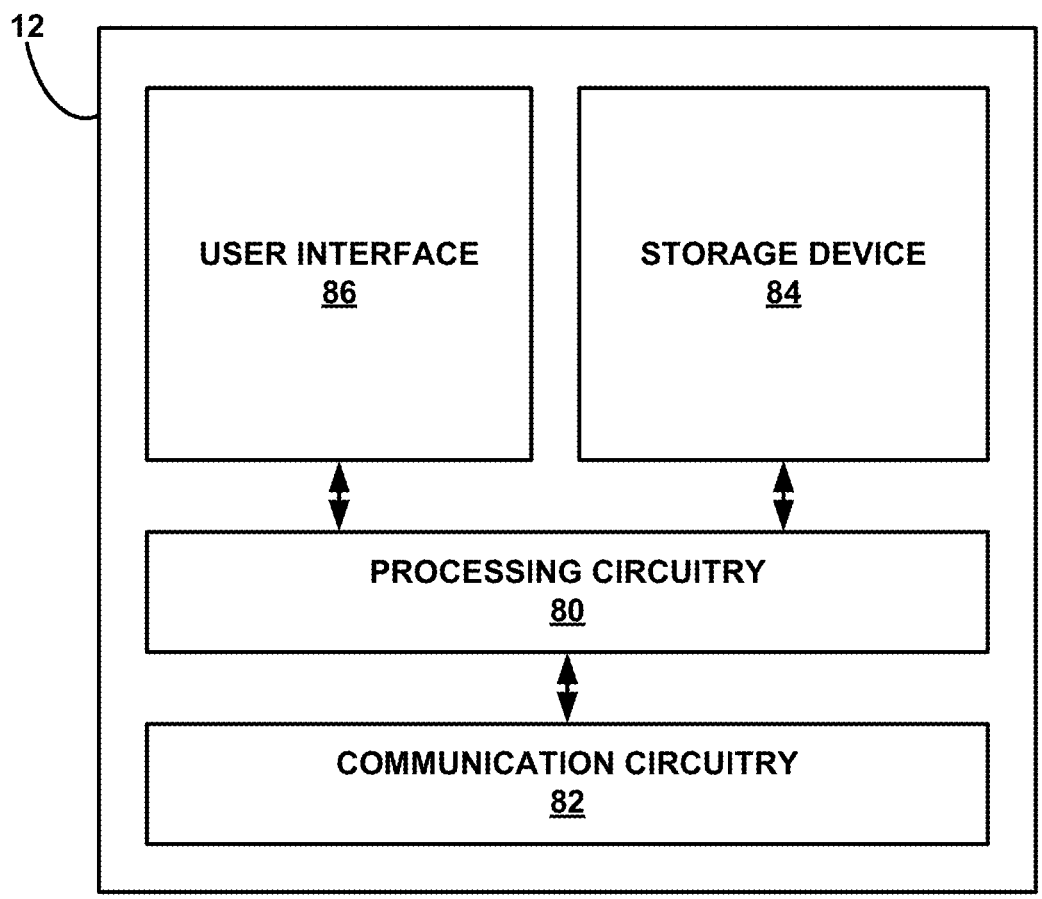
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, Near Field Communication (NFC), Radio Frequency (RF) communication, Bluetooth, Wi-Fi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. Storage device may be used to store at least a portion of a cardiac EGM signal associated with one or more PVCs, morphological information about PVCs, a count or other quantification of PVCs, and/or other cardiac EGM information received from IMD 10. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, external device may receive data from IMD 10, including at least a portion of a cardiac EGM signal associated with one or more PVCs, morphological information about PVCs, a count or other quantification of PVCs (e.g., totals and/or by classification), and/or other cardiac EGM information, for example. In some examples, processing circuitry 80 may transmit an instruction to 1 MB 10 which requests 1 MB 10 to export collected data (e.g., at least a portion of a cardiac EGM signal associated with one or more PVCs, morphological information about PVCs, a count or other quantification of PVCs, and/or other cardiac EGM information) to external device 12. Either way, external device 12 may receive the collected data from IMD 10 and store the collected data in storage device 84. Processing circuitry 80 may implement any of the techniques described herein to analyze cardiac EGMs received from IMD 10, e.g., to determine whether PVC storage criteria is met to store the collected data from 1 MB 10 or to transmit the collected data from IMD 10 and/or other PVC data (e.g., at least a portion of a cardiac EGM signal associated with one or more PVCs, morphological information about PVCs, a count or other quantification of PVCs, and/or other cardiac EGM information) to transmit to another device (e.g., a server, cloud, data center) over a network.

Figure 10:
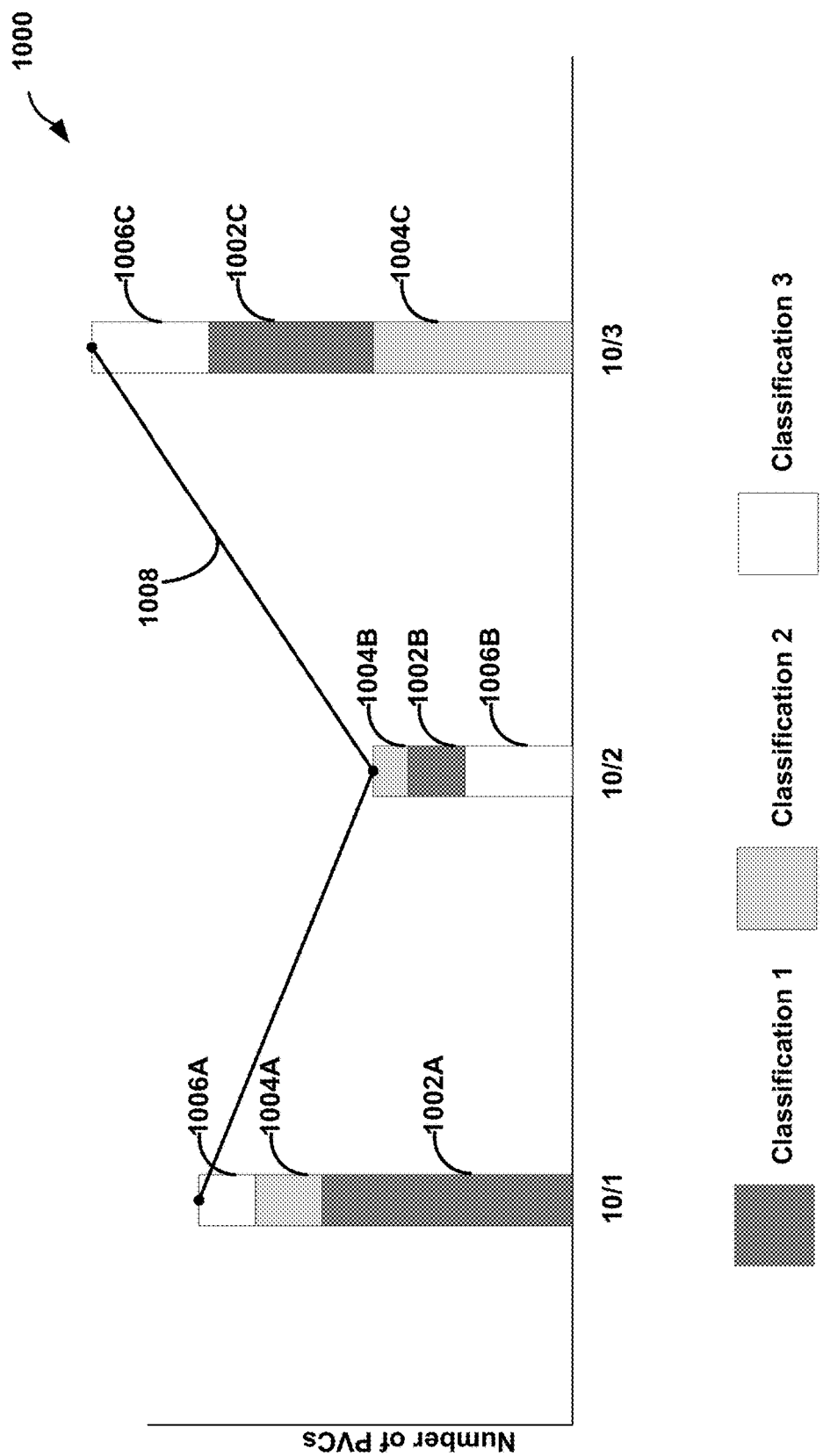
FIG. 10 is a graph illustrating example PVC information that may be presented to a user.

A user, such as a clinician or patient 4, may interact with external device 12 through user interface 86. User interface 86 includes a display system (not shown), such as a liquid crystal display (LCD) or a light emitting diode (LED) display or other type of screen, with which processing circuitry 80 may present information related to IMD 10, e.g., cardiac EGM signals, indications of detections of PVCs, PVC morphology information, and quantifications of detected PVCs, such as a quantification of PVC burden. As described in further detail below, FIG. 10 illustrates exemplary PVC information that may be presented to a user. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 5:
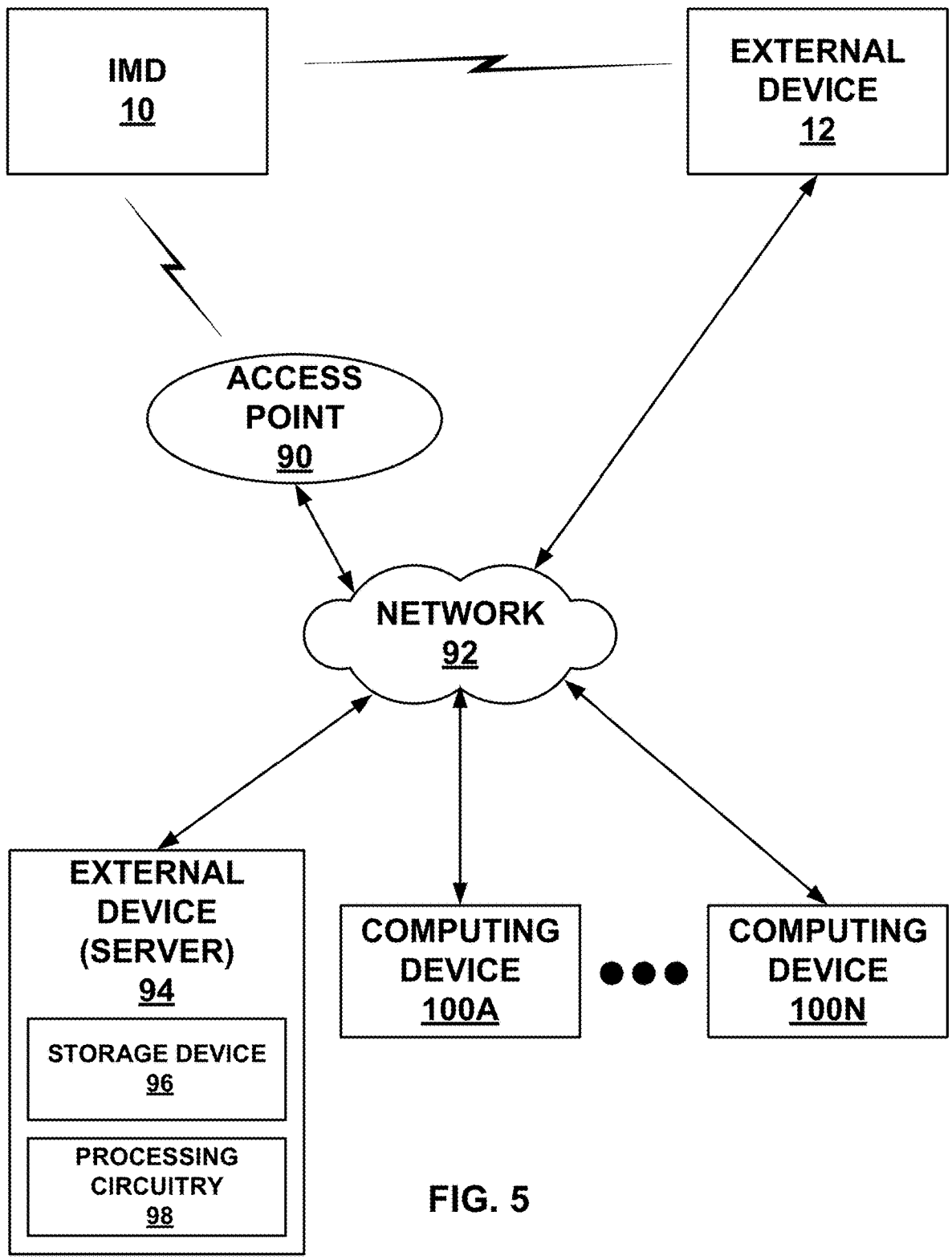
FIG. 5 is a block diagram illustrating an example system that includes an access point, a network, external computing devices, such as a server, and one or more other computing devices, which may be coupled to the IMD and external device of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 or external device 12 may be configured to transmit data, such as PVC detection information, PVC morphology information, PVC quantifications (e.g., PVC burden), and/or cardiac EGM signals, to access point 90 in response to PVC storage criteria being met. Access point 90 may then communicate the received data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network. In some examples, server 94 may comprise one or more servers, a cloud, one or more databases, and/or a data center.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in in between clinician visits, to check on a status of a medical condition. In some examples, the clinician may enter instructions for a medical intervention for patient 4 into an application executed by computing device 100, such as based on a status of a patient condition determined by IMD 10, external device 12, server 94. or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in memory 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze cardiac EGMs received from IMD 10, e.g., to determine whether to store or transmit cardiac EGM information associated with a PVC in response to one or more PVC storage criteria being met.

Storage device 96 may include a computer-readable storage medium or computer-readable storage device. In some examples, memory 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

FIG. 6A is a graph illustrating a cardiac EGM signal 120 and an example technique for detecting and classifying PVCs based on the cardiac EGM signal. For example, the techniques of this disclosure may use different features such as inter-depolarization (e.g., R-R) interval and morphology characteristics to distinguish a PVC depolarization from a normal ventricular depolarization. IMD 10 senses cardiac EGM signal 120 and detects the timing of ventricular depolarizations 122A, 122B, 122C, and 122D (collectively, "ventricular depolarizations 122") using ventricular depolarization, e.g., R-wave, detection techniques such as those described with respect to FIG. 2.

In some examples, IMD 10 senses ventricular depolarizations 122 using two or more, e.g., primary and secondary, sensing channels. The different sensing channels may have different hardware, different firmware settings, and/or different software settings for processing cardiac EGM signal 120 to detect ventricular depolarizations 122. For example, a primary sensing channel may implement a relatively shorter blanking, e.g., 150 milliseconds (ms), auto-adjusting threshold having relatively higher amplitudes for depolarization detection. For the primary sensing channel, some examples may implement the techniques described in U.S. Pat. No. 7,027,858, by Cao et al., which is incorporated herein by reference.

However, because the ventricular depolarization wave, e.g., QRS complexes, of PVC depolarizations (i.e., PVCs) are typically wider and have relatively lower frequency content than normal depolarizations, the primary sensing channel may under sense PVC depolarizations. A secondary sensing channel may include a relatively longer blanking, e.g., 520 ms, fixed threshold, which may facilitate detection of PVC depolarizations that may have not been detected by the primary sensing channel. Processing circuitry 50 and/or sensing circuitry 52 may determine the fixed threshold used by the secondary sensing channel to detect a depolarization in a given cardiac cycle based on amplitudes of one or more prior ventricular depolarizations.

Characteristics that distinguish PVC depolarizations from normal ventricular depolarizations include: shorter intervals between a PVC depolarization and the preceding adjacent (in time) depolarization; longer intervals between a PVC depolarization and a subsequent adjacent depolarization; and differing depolarization and repolarization wave morphologies as between PVC depolarizations and normal ventricular depolarizations. In order to determine whether a current ventricular depolarization 122C is a PVC depolarization, processing circuitry 50 of IMD 10 or other processing circuitry of system 2 may consider interval and morphological information for current ventricular depolarization 122C, preceding (in time) adjacent depolarization 122B, and subsequent (in time) adjacent depolarization 122D. The processing circuitry may iteratively determine whether each of ventricular depolarizations 122 is a PVC depolarization in this manner by proceeding to the next depolarization, e.g., depolarization 122C becomes the preceding adjacent depolarization, depolarization 122D becomes the current depolarization, and the next (in time) depolarization after depolarization 122D becomes the subsequent adjacent depolarization. Although the techniques for determining whether a ventricular depolarization is a PVC depolarization are described herein primarily as being performed by processing circuitry 50 of IMD 10, such techniques may be performed, in whole or part, by processing circuitry of any one or more devices of system 2, such as processing circuitry 80 of external device 12, processing circuitry 98 of server 94, or processing circuitry of one or more computing devices 100.

In some examples, processing circuitry 50 determines respective inter-depolarization intervals 124A-124C (collectively "inter-depolarization intervals 124"), e.g., R-R intervals, for each of depolarizations 122. For example, processing circuitry 50 may determine inter-depolarization interval 124A for preceding adjacent depolarization 122B as the interval between the time of detection of ventricular depolarization 122A and the time of detection of ventricular depolarization 122B. Similarly, processing circuitry 50 may determine inter-depolarization interval 124B for current depolarization 122C as the interval between the time of detection of ventricular depolarization 122B and the time of detection of ventricular depolarization 122C, and inter-depolarization interval 124C for subsequent adjacent depolarization 122D as the interval between the time of detection of ventricular depolarization 122C and the time of detection of ventricular depolarization 122D.

Processing circuitry 50 may also identify respective segments of a digitized version of cardiac EGM signal 120 for each of ventricular depolarizations 122B-122D within respective windows 126A-126C (collectively "windows 126"). Each of windows 126 may include a predetermined number of samples, e.g., sixteen samples sampled at 64 Hz, of cardiac EGM signal 120. The locations of the windows 126 and, thus, which samples of cardiac EGM signal 120 are within a given window 126, may be set relative to the time point at which processing circuitry 50 detected the corresponding ventricular depolarization 122, or another fiducial marker of cardiac EGM signal 120. In some examples, each of windows 126 includes sixteen samples of cardiac EGM signal 120 starting four samples before the point of detection of the respective depolarization 122.

To determine whether current ventricular depolarization 122C is a PVC depolarization, processing circuitry 50 may determine whether ventricular depolarizations 122B-122D satisfy one or more morphological criteria based on the segments within respective windows 126. For each of depolarizations 122B-122D, processing circuitry 50 may determine, as examples, one or more of a maximum amplitude, a minimum amplitude, a maximum slope, and a minimum slope within the respective window 126A-126C. Processing circuitry 50 may determine the time interval, e.g., number of samples, also referred to herein as the slope interval, between the point of the maximum slope and the point of the minimum slope for each of depolarizations 122B-122D. Processing circuitry 50 may determine the slope of cardiac EGM signal 120 using any known techniques, such as by determining a derivative or differential signal of cardiac EGM signal 120.

The morphological criteria may include criteria relating the degree of correlation between the various possible pairings of depolarizations 122B-122D. Processing circuitry 50 may determine correlation values for a pair of depolarizations by performing a correlation operation with the segments of cardiac EGM signal 120 within the respective windows 126 for the depolarizations. Example correlation operations include any known cross-correlation, wavelet-based comparison, feature set comparison, or difference sum techniques.

An example formula for computing cross correlation is:

$$C_{xy}(L) = \frac{1}{Norm} \sum_{k=0}^{N-|L|-1} (x_{k+|L|} - \bar{x})(y_k - \bar{y}) \quad \text{Equation 1}$$

where x and y are the two segments of cardiac EGM signal 120 to be compared and different values of L are the different lags over which the cross-correlation is computed. This equation represents shifting one of the segments by a lag (L), multiplying it with the other segment point-by-point, and adding the multiplied result point-by-point. The same process is followed for different lags. In some examples, the lags are +/− four samples. The maximum of C(L) will happen at the lag where the two segments x and y match the best with each other. In such examples, processing circuitry 50 may determine the maximum of C(L) as the correlation value for a given comparison between two ventricular depolarizations 122.

In order to conserve the processing and power resources of 1 MB 10, processing circuitry 50 may implement a difference sum technique for determining correlation values representative of the degree of correlation between the various pairings of depolarizations 122B-122D. Processing circuitry 50 may determine a point-by-point difference between the segments of cardiac EGM signal 120 for the two depolarizations 122 at various lags, such as +/− four samples, and the lag which has the lowest difference sum will have the highest correlation between the depolarizations 122. An example formula for computing the difference sum is:

$$D_{xy}(L) = \sum_{k=0}^{N-|L|-1} x_{k+|L|} - y_k \quad \text{Equation 2}$$

where x and y are the two segments of cardiac EGM signal 120 to be compared and different values of L are the different lags over which the difference sum is computed. In contrast to C(L), the lowest difference sum value D(L) will occur at the lag where the two segments x and y match best with each other. In other words, the lag with the greatest degree correlation between segments x and y will have the lowest difference sum value D(L).

In some examples, to determine whether current ventricular depolarization 122C is a PVC depolarization (e.g., to detect a PVC), processing circuitry 50 determines a correlation value between current ventricular depolarization 122C and each of preceding adjacent ventricular depolarization 122B and subsequent adjacent depolarization 122D. In the example illustrated by FIG. 6, current ventricular depolarization 122C is a PVC depolarization and both adjacent ventricular depolarizations 122B and 122D are normal ventricular depolarizations. Since ventricular depolarization 122C has a different morphology than both of adjacent ventricular depolarizations 122B and 122D, the correlation values determined by processing circuitry 50 for these two comparisons are both expected to indicate a relatively low degree of correlation, e.g., a relatively high difference sum value. Processing circuitry 50 may also determine a correlation value between adjacent ventricular depolarizations 122B and 122D. Since ventricular depolarizations 122B and 122D are both normal ventricular depolarizations expected to have similar morphologies, the correlation value between them is expected to indicate a relative high degree of correlation, e.g., a relatively low difference sum value. Processing circuitry 50 may apply any combination of one or more of the morphological criteria described herein.

To determine whether current ventricular depolarization 122C is a PVC depolarization, processing circuitry 50 may also evaluate the respective inter-depolarization intervals 124A-124C for ventricular depolarizations 122B-122D. Since current ventricular depolarization 122C is a PVC depolarization, inter-depolarization interval 124B is expected to be shorter than inter-depolarization interval 124A and inter-depolarization interval 124C is expected to be longer than inter-depolarization interval 124A due to a compensatory pause following the PVC depolarization. Processing circuitry 50 may also evaluate the maximum and minimum amplitudes, and the slope intervals, for ventricular depolarizations 122B-122D to determine whether depolarization 122C is a PVC depolarization. Since depolarization 122C is a PVC depolarization and is expected to have a wide QRS complex, the interval, e.g., number of samples, between the maximum and minimum slope for depolarization 122C is expected to be more than that of a normal depolarization, such as adjacent depolarizations 122B and 122D. For PVC detection, some examples may implement the techniques described in U.S. Pat. No. 9,675,270, by Sarkar; U.S. Patent Pub. Nos. 2016/0310029 and 2016/0310031, by Sarkar; and U.S. patent application Ser. No. 16/436,012, by Rajagopal et al., which are incorporated herein by reference.

After determining that current ventricular depolarization 122C is a PVC depolarization, processing circuitry 50 may classify current ventricular depolarization 122C. For example, processing circuitry 50 may store a plurality of classifications in storage device 56. In the example shown in FIG. 6A, storage device 56 may contain classifications 1, 2, and 3 represented by PVC morphologies 127A, 128A, and 129A, respectively. In some examples, each of PVC morphologies 127A, 128A, and 129A may comprise the average or mean morphology of the PVC signals detected under the corresponding classification. In other examples, each of the of PVC morphologies 127A, 128A, and 129A may comprise the last PVC signal classified under the corresponding classification.

To classify ventricular depolarization 122C or the portion of EGM signal 120 associated with ventricular depolarization 122C (e.g., the portion of EGM signal 120 contained within window 126B) (herein referred to as "PVC 122C"), processing circuitry 50 may determine a difference between PVC 122C and each of PVC morphologies 127A, 128A, and 129A to identify the closest classification to PVC 122C. For example, processing circuitry 50 may determine correlation values between PVC 122C and each of PVC morphologies 127A, 128A, and 129A. To determine these correlation values, processing circuitry 50 may perform any of the correlation operations described above (e.g., cross correlation, wavelet-based comparison, feature set comparison, or difference sum techniques). For example, processing circuitry 50 may determine correlation values between PVC 122C and each of PVC morphologies 127A, 128A, and 129A using the difference sum technique to identify the closest classification (e.g., the classification with the lowest difference sum). In some examples, processing circuitry 50 can determine the Euclidean distance between PVC 122C and each of the PVC morphologies to identify the closest classification (e.g., the PVC morphology with the lowest Euclidean distance to PVC 122C). An example formula for computing a Euclidean distance is:

$$d = \sqrt{(x_2-x_1)^2 + (y_2-y_1)^2} \quad \text{Equation 3}$$

where x and y are the two points of PVC 122C and a stored PVC morphology. In some examples, processing circuitry 50 may determine N Euclidean distances between N different points on PVC 122C and each stored PVC morphology and either add the N Euclidean distances or calculate the average Euclidean distance to determine the correlation value between PVC 122C and each stored PVC morphology. Either way, the PVC morphology with the lowest Euclidean distance will represent the closest stored classification to PVC 122C. In some examples, processing circuitry 50 may classify PVC 122C using a clustering algorithm, such as K-Means clustering, for example.

In the example shown in FIG. 6A, processing circuitry 50 may determine PVC morphology 128A as the closest classification to PVC 122C after determining the correlation values (e.g., the difference sum) between PVC 122C and each of PVC morphologies 127A, 128A, and 129A, and finding that the correlation value of PVC morphology 128A is the lowest of the three correlation values. While only three classifications are shown in FIG. 6A, processing circuitry 50 may store fewer or more classifications in accordance with this disclosure. For example, processing circuitry 50 may store any number (N) classifications, and processing circuitry 50 would determine N correlation values between PVC 122C and each of the N classifications to identify the closest classification (e.g., the classification with the lowest difference sum). Processing circuitry 50 may then determine whether the correlation value (e.g., the difference sum) between PVC 122C and PVC morphology 128A is below a threshold value. If the correlation value is equal to or above the threshold value, processing circuitry 50 will classify PVC 122C as a new classification (e.g., "Classification 4") and optionally store PVC 122C as the PVC morphology for that new classification. If the correlation value is below the threshold value, processing circuitry 50 will classify PVC 122C under "Classification 2." In some examples, when the PVC morphology 128A represents the average or mean morphology of the PVC signals detected under "Classification 2," processing circuitry 50 will update PVC morphology 128A (e.g., recalculate the mean or average PVC morphology) to include the morphology of PVC 122C (e.g., as shown in PVC morphology 128AA of FIG. 6B) if PVC 122C is classified as "Classification 2."

FIG. 6B illustrates exemplary classified PVC cardiac EGM signals. In particular, FIG. 6B shows classifications 1, 2, and 3 represented by PVC morphologies 127A, 128AA, and 129A, respectively. While only three classifications are shown in FIG. 6B, processing circuitry 50 may store fewer or more classifications in accordance with this disclosure. In this example, each of PVC morphologies 127A, 128AA, and 129A comprise the average or mean morphology of the PVC signals detected under the corresponding classification. For example, PVC morphology 127A represents the average or mean of PVC signals 127B, 127C, and 127D; PVC morphology 128AA represents the average or mean of PVC signals 128B, 128C, 128D, and PVC 122C of FIG. 6A; and PVC morphology 129A represents the average or mean of PVC signals 129B and 129C. In some examples, PVC morphology 128AA may include PVC 122C of FIG. 6A. In some examples, each of PVC signals 127B, 127C, 127D, 128B, 128C, 128D, 129B, and 129C comprise portions of a cardiac EGM signal corresponding to a PVC (e.g., the P, QRS, and T waves of the PVC).

In some examples, processing circuitry 50 stores each of PVC signals 127A, 127B, 127C, 127D, 128AA, 128B, 128C, 128D, 129A, 129B, and 129C in storage device 56. For example, processing circuitry 50 may store each of PVC signals 127A, 128AA, and 129A in a buffer in storage device 56. In some examples, each buffer includes a reference to a data structure (e.g., stack, queue, array, linked list, tree, or table), containing the PVC signals detected under the corresponding classification. For example, the buffer entry containing PVC morphology 127A may include a reference or link to a data structure containing PVC signals 127B, 127C, and 127D; the buffer entry containing PVC morphology 128AA may include a reference or link to a data structure containing PVC signals 128B, 128C, and 128D; and the buffer entry containing PVC morphology 129A may include a reference or link to a data structure containing PVC signals 129B and 129C. In some examples, processing circuitry 50 may store all or the last N number (e.g., 10, 20) of PVC signals detected under the corresponding classification. In the examples where processing circuitry 50 store only the last N number (e.g., 10, 20) of PVC signals and the N number of PVC signals are stored for a particular classification, the processing circuitry removes the oldest stored PVC signal before storing another PVC signal. In some examples, stored PVC signals are purged automatically after a certain period of time (e.g., after a week, a month, a year, or any other period of time) or manually by the user, a physician, or an admin.

In some examples, processing circuitry 50 stores each of PVC signals 127A, 127B, 127C, 127D, 128AA, 128B, 128C, 128D, 129A, 129B, and 129C in a cloud (e.g., external device 12 and/or 94). In some examples, the cloud may periodically (e.g., every week, month, year, or any other period of time) update the average or mean morphology of the last N number (e.g., 10, 20) of stored PVC signals. In some examples, the cloud may not purge any stored PVC signals.

In some examples, if a particular classification may not match to any detected PVC for a sufficiently long period of time (e.g., a 3 months, 6 months, a year, or any other period of time), processing circuitry 50 may "retire" or "archive" that classification (e.g., processing circuitry 50 may no longer compare future detected PVCs to that classification) as it may not be applicable anymore to the clinical situation at present. For example, processing circuitry 50 may keep track of how many matches are being generated for a given classification and when the PVCs were detected.

Figure 7:
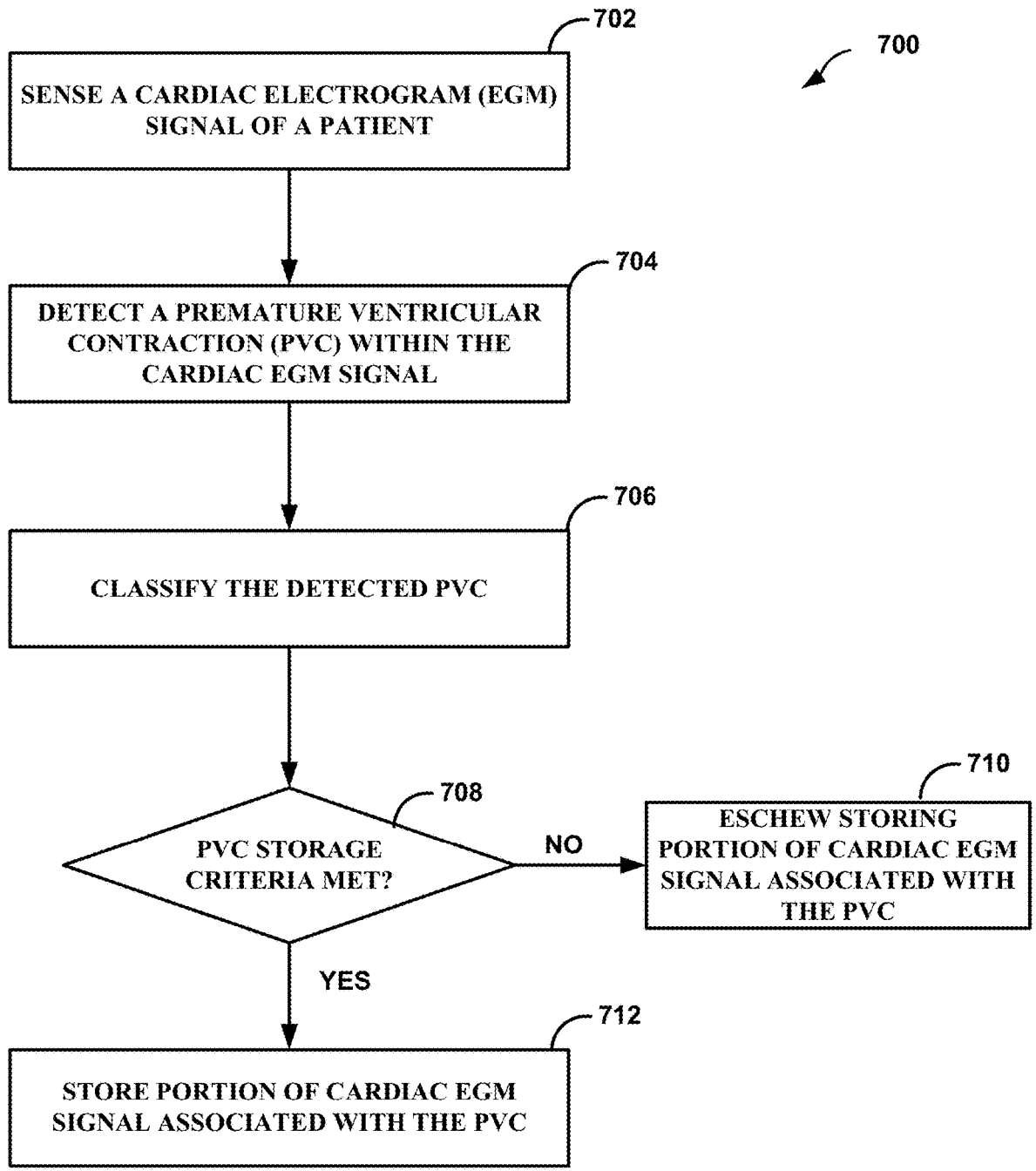
FIG. 7 is a flow diagram illustrating an example operation for triggering the storage of a cardiac EGM signal associated with a PVC.

FIG. 7 is a flow diagram illustrating an example operation for triggering the storage of a cardiac EGM signal associated with a PVC. Although the example operation of FIG. 7 is described as being performed by processing circuitry 50 of 1 MB 10 and with respect to cardiac EGM signal 120 of FIG. 6, in other examples some or all of the example operation may be performed by processing circuitry of another device and with respect to any cardiac EGM.

According to the example of FIG. 7, processing circuitry 50 senses a cardiac EGM signal of a patient (e.g., via electrodes 16) (702). Next, processing circuitry 50 detects a PVC within the cardiac EGM signal (e.g., as described above with reference to FIG. 6A or any other known method of detecting PVCs within a cardiac EGM signal) (704). In some examples, processing circuitry 50 keeps a count of detected PVCs for a period of time (e.g., 6 hours, 24 hours, a week, a month).

Processing circuitry 50 then classifies the detected PVC (706). As described above with reference to FIG. 6A, to classify PVC 122C, processing circuitry 50 may compare the morphology of PVC 122 to each of PVC morphologies 127A, 128A, and 129A corresponding to the classifications stored in storage device 56 to identify the closest classification to PVC 122C. If the difference between PVC 122C and the closest classification in storage device 56 is equal to above a threshold difference, processing circuitry 50 will create a new classification and store PVC 122C as the PVC morphology for that new classification. If the difference between PVC 122C and the closest classification in storage device 56 is less than a threshold difference, processing circuitry 50 will classification PVC 122C as the closest classification. In some examples, processing circuitry 50 can determine the Euclidean distance between PVC 122C and each of the PVC morphologies to identify the closest classification (e.g., the PVC morphology with the lowest Euclidean distance to PVC 122C). In the example shown in FIG. 6A, PVC morphology 128A is the closest classification to PVC 112C and the difference (e.g., the correlation value) between PVC morphology 128A and PVC 112C is below a threshold value and processing circuitry 50 classifies PVC 122C under "Classification 2." In some examples, when the PVC morphology 128A represents the average or mean morphology of the PVC signals detected under "Classification 2," processing circuitry 50 will update PVC morphology 128A (e.g., recalculate the mean or average PVC morphology) to include the morphology of PVC 122C (e.g., as shown in PVC morphology 128AA of FIG. 6B). In some examples, processing circuitry 50 may classify PVC 122C using a clustering algorithm, such as K-Means clustering, for example. In some examples, processing circuitry 50 keeps a count of detected or other quantification of the PVCs detected for a given classification (e.g., determines a PVC burden by classification).

Processing circuitry 50 further determines whether the PVC storage criteria is met (708). In some examples, PVC storage criteria is met if the PVC burden exceeds a PVC burden threshold, if a new PVC classification is detected, if a bigeminy or trigeminy event is detected, or if an R-on-T phenomenon is detected (e.g., as described in further detail below with reference to FIG. 8).

Based on a determination that PVC storage criteria is not met (NO branch of 708), processing circuitry 50 may eschew storing the portion of cardiac EGM signal 120 associated with PVC 122C (710). Based on a determination that PVC storage criteria is met (YES branch of 708), processing circuitry 50 may store the portion of cardiac EGM signal 120 associated with PVC 122C (712). For example, processing circuitry 50 may store the portion of cardiac EGM signal 120 associated with PVC 122C in storage device 56. In some examples, processing circuitry 50 stores PVC 122C with other PVCs occurring within a first period of time (e.g., 24 hours, a week, a month). In some examples, processing circuitry 50 may transmit the portion of cardiac EGM signal 120 associated with PVC 122C to another device via a network in response to a determination that PVC storage criteria is met (YES branch of 708). For example, processing circuitry 50 may transmit the portion of cardiac EGM signal 120 associated with PVC 122C to external device 12, server 94, any of computing devices 100, or any other device. In other examples, the portion of cardiac EGM signal 120 associated with PVC 122C may include one or more other beats around the PVC 122C. For example, processing circuitry 50 may store or transmit a portion of the cardiac EGM signal including PVC 122C with a duration between two and fourteen minutes. In some examples, processing circuitry 50 may store or transmit other PVC information, including PVC burden information (e.g., total and/or by classification) for a given duration of time (e.g., 24 hours, a week, a month) or timing information (e.g., start and end time), for example.

Figure 8:
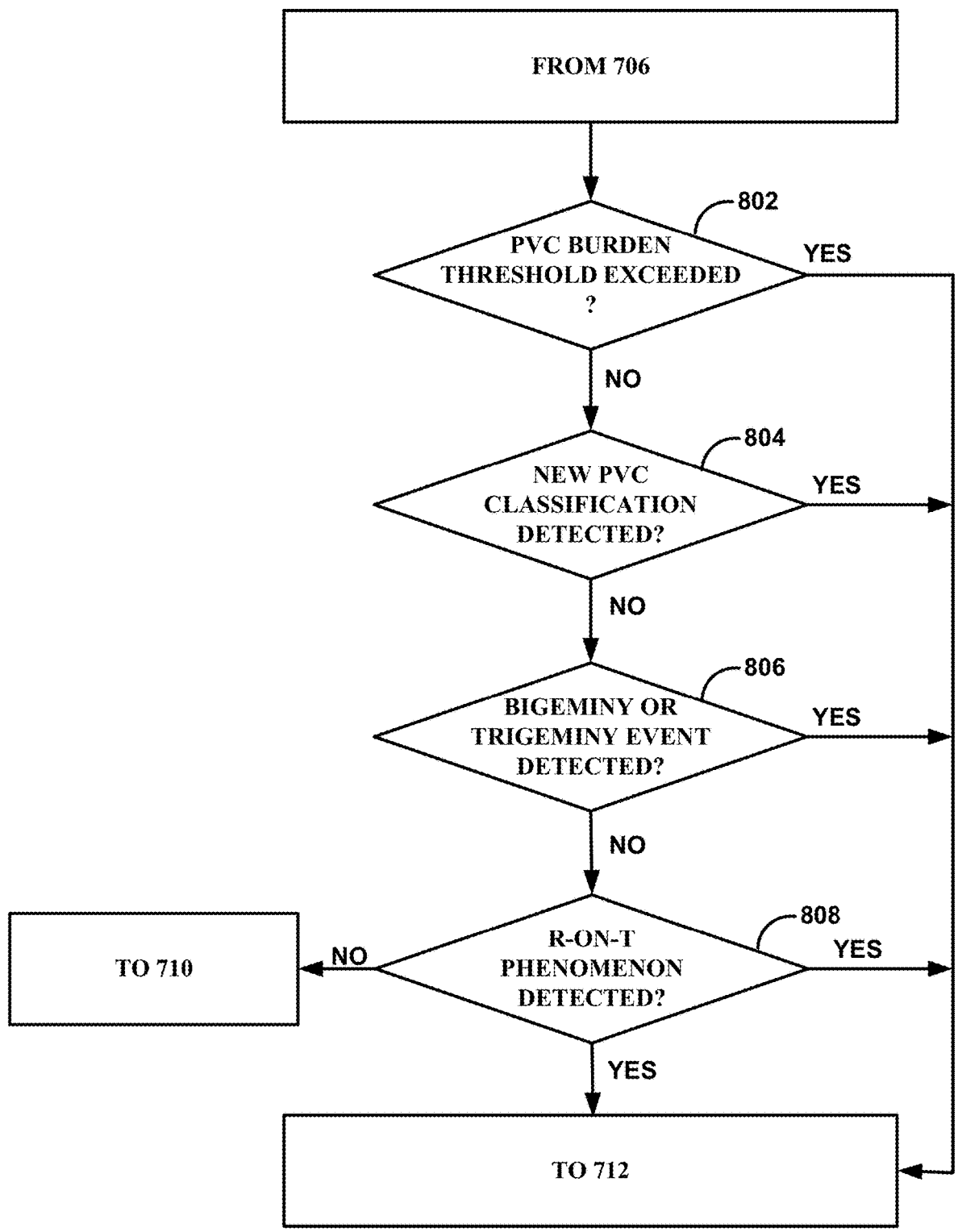
FIG. 8 is a flow diagram illustrating an example operation for triggering the storage of a portion of a cardiac EGM signal associated with a PVC.

FIG. 8 is a flow diagram illustrating an example operation for triggering the storage of a portion of a cardiac EGM signal associated with a PVC. The example operation of FIG. 8 may be an example implementation of element 708 of FIG. 7, and is illustrated as beginning from element 706. In other examples, the example operation of FIG. 8 may be performed as part of another method for triggering the storage of a portion of a cardiac EGM signal associated with a PVC. In some examples, elements 802-808 may be performed in any order. In some examples, one or more of elements 802-802 need not be performed.

According to the example of FIG. 8, processing circuitry 50 determines whether a PVC burden threshold is exceeded (802). In some examples, processing circuitry 50 may determine that PVC burden threshold is exceeded if it is above 10% of a period a time (e.g., 6 hours, 12 hours, 24 hours, a week, a month). In some examples, processing circuitry 50 will determine a PVC burden for all detected PVCs. In some examples, processing circuitry 50 will determine a PVC burden for each PVC classification stored in storage device 56. For example, processing circuitry 50 will determine a total PVC burden, a first PVC burden for Classification 1 (PVC morphology 127A), a second PVC burden for Classification 2 (PVC morphology 128A or 128AA), and a third PVC burden for Classification 3 (PVC morphology 129A). In this way, processing circuitry 50 will determine whether any of the total, first, second, or third PVC burdens exceeds the PVC burden threshold (802). Either way, if a PVC burden threshold is exceeded (YES branch of 802), processing circuitry 50 will store the portion of cardiac EGM signal 120 associated with the detected PVC (712).

If processing circuitry 50 determines that the PVC burden threshold is not exceeded (NO branch of 802), processing circuitry 50 determines whether a new PVC classification is detected (804). As described above with reference to FIG. 6A, processing circuitry 50 will detect a new classification if the closest existing classification to the detected PVC is too different. For example, if the correlation value (e.g., the difference sum) between PVC 122C and PVC morphology 128A is equal to or above a threshold value in the example in FIG. 6A, processing circuitry 50 will classify PVC 122C as a new classification (e.g., "Classification 4"). If a new PVC classification is detected (e.g., because the correlation value between the detected PVC and the closest classification stored in storage device 56 it too great) (YES branch of 804), processing circuitry 50 will store the portion of cardiac EGM signal 120 associated with the detected PVC (712).

If processing circuitry 50 determines that a new PVC classification is not detected (NO branch of 804), processing circuitry 50 determines whether a bigeminy or trigeminy event is detected in a cardiac EGM signal (806). Processing circuitry 50 will detect a bigeminy event in a cardiac EGM signal if each detected normal beat is followed by a PVC or by any other abnormal beat. For example, a beat pattern in a cardiac EGM signal comprising a normal beat, a PVC, a normal beat, a PVC, and so on would constitute a bigeminy event (whether or not the detected PVCs are of the same or different classifications). Processing circuitry 50 will detect a trigeminy event in a cardia EGM signal if processing circuitry 50 detects two normal beats followed by a PVC or if processing circuitry 50 detects a normal beat followed by two PVCs (YES branch of 806). For example, to detect the bigeminy event in cardiac EGM signal 120, processing circuitry 50 may determine that current depolarization 122C is a PVC and determine whether the previous two depolarizations (e.g., depolarizations 122A and 122B) were a PVC and a normal beat, respectively (whether or not the detected PVCs are of the same or different classifications). In the example shown in FIG. 6A, processing circuitry 50 may detect a bigeminy event in cardiac EGM signal 120 because ventricular depolarization 122A is a PVC depolarization, ventricular depolarization 122B is a normal depolarization, and ventricular depolarization 122C is a PVC. In some examples, processing circuitry 50 may determine whether a quadrigeminy event occurs at element 806. Processing circuitry 50 will detect a quadrigeminy event in a cardia EGM signal if each detected normal beat is followed by three consecutive PVCs or if every fourth beat is a PVC (whether or not the detected PVCs are of the same or different classifications). In some examples, processing circuitry 50 may determine whether a couplet event occurs at element 806 if processing circuitry 50 detects two consecutive PVCs in a cardiac EGM signal (whether or not the detected PVCs are of the same or different classifications). In some examples, processing circuitry 50 may determine whether a triplet event occurs at element 806 if processing circuitry 50 detects three consecutive PVCs in a cardiac EGM signal (whether or not the detected PVCs are of the same or different classifications). If a bigeminy, a trigeminy, a quadrigeminy, a couplet, or a triplet event is detected in a cardiac EGM signal (YES branch of 806), processing circuitry 50 will store the portion of cardiac EGM signal 120 associated with the detected PVCs (712).

If processing circuitry 50 determines that a bigeminy or trigeminy is not detected in a cardiac EGM signal (NO branch of 806), processing circuitry 50 determines whether an R-on-T phenomenon is detected (808). Processing circuitry 50 will detect an R-on-T phenomenon when it detects a PVC (e.g., a PVC depolarization) on the T-wave of the previous beat in the cardiac EGM signal. An R-on-T phenomenon is a particularly dangerous event because ventricular fibrillation and death can occur. During the T-wave (repolarization), the heart muscle is very sensitive to outside stimulus and a strong PVC can send the myocardium into fibrillation. If an R-on-T phenomenon is detected in a cardiac EGM signal (YES branch of 808), processing circuitry 50 will store the portion of cardiac EGM signal 120 associated with the detected PVC (712). In some examples, processing circuitry 50 will generate an automated clinician alert in response to detecting an R-on-T phenomenon. If processing circuitry 50 determines that an R-on-T phenomenon is not detected in a cardiac EGM signal (NO branch of 808), processing circuitry 50 may eschew storing the portion of cardiac EGM signal 120 associated with the detected PVC (710).

Figure 9:
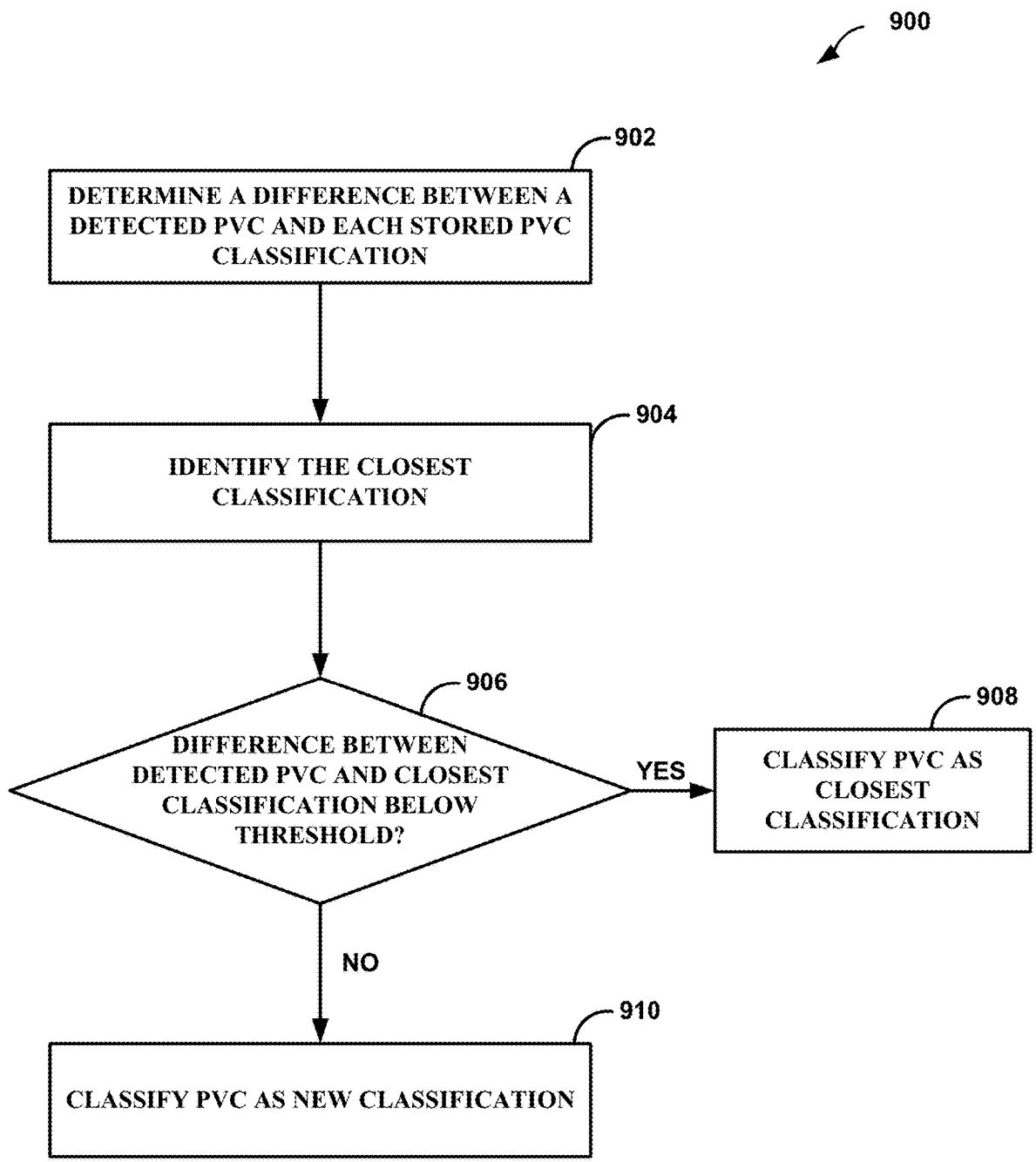
FIG. 9 is a flow diagram illustrating an example operation for classifying PVCs.

In some examples, processing circuitry 50 may determine whether one or more of criteria 802-808 are met. For example, processing circuitry 50 may perform elements 802-808 for every detected PVC. In that example, processing circuitry 50 will store which of criteria 802-808 are met in addition to storing the portion of cardiac EGM signal 120 associated with the detected PVC. For example, if a PVC burden threshold is exceeded (YES branch of 802), processing circuitry 50 may store an indication that the PVC burden was exceeded and determines whether a new PVC classification is also detected (804). If processing circuitry 50 determines that a new PVC classification is detected (YES branch of 804), processing circuitry 50 may store an indication that a new PVC classification was detected and also determines whether a bigeminy or trigeminy event is detected in a cardiac EGM signal (806). If processing circuitry 50 determines that a bigeminy, trigeminy, quadrigeminy, couplet, or triplet event was detected in a cardiac EGM signal (YES branch of 806), processing circuitry 50 processing circuitry 50 may store the detected PVCs and an indication that bigeminy, trigeminy, quadrigeminy, couplet, or triplet event was detected and also determines whether an R-on-T phenomenon is detected (808). In this example, elements 802-808 could be performed serially, concurrently, or in any order. FIG. 9 is a flow diagram illustrating an example operation for classifying PVCs. The example operation of FIG. 9 may be an example implementation of element 706 of FIG. 7. In other examples, the example operation of FIG. 9 may be performed as part of another method for triggering the storage of a portion of a cardiac EGM signal associated with a PVC.

According to the example of FIG. 9, processing circuitry 50 determines a difference between a detected PVC and each stored PCV classification in storage device 56 (902). As shown in the example in FIG. 6A, storage device 56 may contain classifications 1, 2, and 3 represented by PVC morphologies 127A, 128A, and 129A, respectively. In some examples, processing circuitry 50 may determine a difference between PVC 122C and each of PVC morphologies 127A, 128A, and 129A by determining correlation values between PVC 122C and each of PVC morphologies 127A, 128A, and 129A. To determine these correlation values, processing circuitry 50 may perform any of the correlation operations described above with reference to FIG. 6A (e.g., cross correlation, wavelet-based comparison, feature set comparison, difference sum, or Euclidean distance techniques). For example, processing circuitry 50 may determine correlation values between PVC 122C and each of PVC morphologies using the difference sum technique. Based on the correlation values, processing circuitry 50 then identifies the closest stored classification to PVC 122C (904). In the example shown in FIG. 6A, processing circuitry 50 may identify PVC morphology 128A as the closest classification to PVC 122C (e.g., the classification with the lowest difference sum).

Processing circuitry 50 may then determines whether the difference between the detected PVC and the closest classification is below a threshold value (906). For example, processing circuitry 50 may determine whether the correlation value (e.g., the difference sum) between PVC 122C and PVC morphology 128A is below a threshold value. Based on a determination that the correlation value is equal to or above the threshold value (NO branch of 906), processing circuitry 50 will classify PVC 122C as a new classification (e.g., "Classification 4") and optionally store PVC 122C as the PVC morphology for that new classification (910). Based on a determination that the correlation value is below the threshold value (YES branch of 906), processing circuitry 50 will classify PVC 122C under "Classification 2." In some examples, when the PVC morphology 128A represents the average or mean morphology of the PVC signals detected under "Classification 2," processing circuitry 50 will update PVC morphology 128A (e.g., recalculate the mean or average PVC morphology) to include the morphology of PVC 122C (e.g., as shown in PVC morphology 128AA of FIG. 6B).

FIG. 10 is a graph illustrating example PVC information that may be presented to a user. For example, graph 1000 may comprise a user interface for use by a physician, clinical technician, or any other user to review PVC information classified and stored in accordance with techniques of this disclosure.

In the example shown in FIG. 10, the number of PVCs detected (e.g., the PVC burden) for each day are presented. For example, FIG. 10 illustrates the total PVC burden on each day with line graph 1008. FIG. 10 also illustrates bar graphs with a visual break down of the PVC burden by classification on each day. For example, the per-day PVC burden for Classification 1 is shown by bars 1002A, 1002B, and 1002C (collectively, "bars 1002"); the per-day PVC burden for Classification 2 is shown by bars 1004A, 1004B, and 1004C (collectively, "bars 1004"); and the per-day PVC burden for Classification 3 is shown by bars 1006A, 1006B, and 1006C (collectively, "bars 1006"). While FIG. 10 shows bars 1002, 1004, and 1006 stacked on top of each other in order with the highest PVC burden per day at the bottom and the lowest PVC burden per day at the top, it is understood that each of bars 1002, 1004, and 1006 may be displayed adjacent to each other and/or in any order. In some examples, a physician, clinical technician, or any other user may select any of bars 1002, 1004, and 1006 and the system will display additional PVC information (in the same screen or in a pop up screen). For example, the system may display stored portions of the cardiac EGM signal corresponding to the detected PVCs for that particular day. For example, a user may select bar 1002A and the system may display stored portions of the cardiac EGM signal corresponding to the detected Classification 1 PVCs for 10/1. In this way, the system may help physicians detect and identify patterns of PVCs to better treat their patients, particularly patients with existing heart problems. For example, physicians may want to view and analyze EGM data about the morphologies of the PVCs detected in a particular patient. This may assist a physician to localize the origin of the PVCs and/or determine whether there are multiple triggers causing the PVCs, which may facilitate more accurate determinations of cardiac wellness and risk of sudden cardiac death, and may lead to clinical interventions to suppress PVCs such as medications.

As described above, processing circuitry, such as processing circuitry 50 of IMD 10, may include any combination of one or more of hardware, firmware, and software configured to implement the techniques described herein. In some examples, implementation of certain aspects of the described techniques in hardware may improve the computation and power performance of the implementing device, e.g., IMD 10. As examples, processing circuitry may include hardware configured to compute difference sums or other correlation values, and include firmware for other functionality described herein.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an 1 MB, an external programmer, a combination of an 1 MB and external programmer, an integrated circuit (IC) or a set of ICs, and/or discrete electrical circuitry, residing in an IMD and/or external programmer.

What is claimed is:

1. A system comprising:
   a memory; and
   processing circuitry in communication with the memory, wherein the processing circuitry is configured to:
   identify, in a cardiac signal sensed by a medical device via one or more electrodes, a set of premature ventricular contractions (PVCs) of a heart of a patient;
   determine, for each PVC of the set of PVCs, whether the PVC meets PVC storage criteria, wherein a first one or more PVCs of the set of PVCs meet the PVC storage criteria, and wherein a second one or more PVCs of the set of PVCs do not meet the PVC storage criteria; and
   store, in the memory and for each PVC of the first one or more PVCs that meet the PVC storage criteria, a portion of the cardiac signal corresponding to each PVC of the first one or more PVCs.

2. The system of claim 1, wherein the processing circuitry is further configured to eschew storing a portion of the cardiac signal corresponding to each PVC of the second one or more PVCs that do not meet the PVC storage criteria in the memory.

3. The system of claim 1, further comprising the medical device configured to sense, via the one or more electrodes, the set of PVCs within the cardiac signal.

4. The system of claim 1, wherein the processing circuitry is configured to:
   determine, for each PVC of the set of PVCs, that the PVC storage criteria is met when a PVC burden is above a PVC burden threshold; and
   determine, for each PVC of the set of PVCs that the PVC storage criteria is not met when the PVC burden is equal to or below the PVC burden threshold.

5. The system of claim 4, wherein the PVC burden for each PVC of the set of PVCs comprises a ratio of a number of PVCs of the set of PVCs occurring during a period of time before the PVC to a total number of ventricular contractions occurring during the period of time before the PVC.

6. The system of claim 1, wherein the processing circuitry is further configured to:
   analyze, for each PVC of the set of PVCs, a morphology of the PVC in the cardiac signal; and
   classify each PVC of the set of PVCs based on a set of PVC morphology classifications stored by the memory and the morphology of the PVC in the cardiac signal.

7. The system of claim 6, wherein the processing circuitry is further configured to:
   determine, for each PVC of the set of PVCs, that the PVC storage criteria is met when the PVC is classified into a new PVC morphology classification not previously stored by the memory; and determine, for each PVC of the set of PVCs, that the PVC storage criteria is not met when the PVC is classified into an existing PVC morphology classification of the set of PVC morphology classifications stored by the memory.

8. The system of claim 6, wherein the processing circuitry is further configured to:
    determine, for each PVC of the set of PVCs, a PVC burden for each PVC morphology classification of the set of PVC morphology classifications,
    wherein the PVC burden for each PVC morphology classification of the set of PVC morphology classifications comprises a ratio of a number of PVCs of the set of PVCs classified according to the PVC morphology classification occurring during a period of time before the PVC to a total number of ventricular contractions occurring during the period of time before the PVC.

9. The system of claim 8, wherein the processing circuitry is configured to:
    determine, for each PVC of the set of PVCs, that the PVC storage criteria is met when a PVC burden corresponding to any of the set of PVC morphology classifications is above a PVC burden threshold; and
    determine, for each PVC of the set of PVCs that the PVC storage criteria is not met when the PVC burden corresponding to each PVC morphology classification of the set of PVC morphology classifications is equal to or below the PVC burden threshold.

10. The system of claim 6,
    wherein to analyze the morphology of each PVC in the cardiac signal of the set of PVCs, the processing circuitry is configured to compare the morphology of the PVC in the cardiac signal to each PVC morphology classification of the set of PVC morphology classifications, wherein each PVC morphology classification of the set of PVC morphology classifications comprises a mean morphology of classified according to the PVC morphology classification,
    wherein to classify each PVC in the cardiac signal of the set of PVCs, the processing circuitry is configured to:
        identify a first PVC morphology classification of the set of PVC morphology classifications with a first mean morphology closest to the morphology of the PVC in the cardiac signal;
        calculate a difference between the first mean morphology and the morphology of the PVC in the cardiac signal;
        in response a difference between the first mean morphology and the morphology of the PVC in the cardiac signal being below a threshold difference value:
            classify the PVC corresponding to the first PVC morphology classification and
            update the first mean morphology of the first PVC morphology classification to include the morphology of the PVC in the cardiac signal; and
        in response to the difference between the first mean morphology and the morphology of the PVC in the cardiac signal being equal to or above the threshold difference value:
            classify the PVC according to a new PVC morphology classification; and
            set a new mean morphology of the new PVC morphology classification to the morphology of the PVC in the cardiac signal.

11. The system of claim 6, further comprising a display device configured to display information indicative of one or more PVCs corresponding to each PVC morphology classification of the set of PVC morphology classifications.

12. The system of claim 6, wherein each PVC morphology classification of the set of PVC morphology classifications comprises a representative morphology stored in a buffer,
    wherein to analyze the morphology of each PVC in the cardiac signal of the set of PVCs, the processing circuitry is configured to compare the morphology of the PVC in the cardiac signal to the representative morphology corresponding to each PVC morphology classification of the set of PVC morphology classifications, and
    wherein to classify each PVC in the cardiac signal of the set of PVCs, the processing circuitry is configured to:
        identify a first PVC morphology classification with a first representative morphology closest to the morphology of the PVC in the cardiac signal;
        calculate a difference between the first representative morphology and the morphology of the PVC in the cardiac signal;
        in response to the difference between the first representative morphology and the morphology of the PVC in the cardiac signal being below a threshold difference value, set the first representative morphology to the morphology of the PVC in the cardiac signal; and
        in response to the difference between the first representative morphology and the morphology of the PVC in the cardiac signal being equal to or above the threshold;
            classify the PVC according to a new PVC morphology classification; and
            store the morphology of the PVC in the cardiac signal in a buffer as a new representative morphology for the new PVC morphology classification.

13. The system of claim 1, wherein the portion of the cardiac signal corresponding to each PVC of the first one or more PVCs comprises a portion of the cardiac signal corresponding to the PVC that extends from a first time before an R-wave of the PVC to a second time after the R-wave of the PVC.

14. The system of claim 1, wherein the portion of the cardiac signal corresponding to each PVC of the first one or more PVCs comprises a portion of the cardiac signal corresponding to the PVC including the PVC and two or more ventricular contractions occurring around the PVC.

15. The system of claim 1, wherein the portion of the cardiac signal corresponding to each PVC of the first one or more PVCs comprises a portion of the cardiac signal corresponding to the PVC including the PVC with a duration between two and fourteen minutes.

16. The system of claim 1, wherein the processing circuitry is configured to determine, for each PVC of the set of PVCs, that the PVC storage criteria is met when the PVC is part of a Bigeminy, Trigeminy, Quadrigeminy, Couplet, or Triplet event.

17. The system of claim 1, wherein the processing circuitry is configured to determine, for each PVC of the set of PVCs, that the PVC storage criteria is met when the PVC corresponds to an R-on-T phenomenon.

18. A method comprising:
    identifying, by processing circuitry in communication with a memory in a cardiac signal sensed by a medical device via one or more electrodes, a set of premature ventricular contractions (PVCs) of a heart of a patient;

determining, by the processing circuitry for each PVC of the set of PVCs, whether the PVC meets PVC storage criteria, wherein a first one or more PVCs of the set of PVCs meet the PVC storage criteria, and wherein a second one or more PVCs of the set of PVCs do not meet the PVC storage criteria; and storing, by the processing circuitry in the memory and for each PVC of the first one or more PVCs that meet the PVC storage criteria, a portion of the cardiac signal corresponding to each PVC of the first one or more PVCs.

19. The method of claim 18, further comprising eschewing, by the processing circuitry, storing a portion of the cardiac signal corresponding to each PVC the second one or more PVCs that do not meet the PVC storage criteria in the memory.

20. A non-transitory computer-readable medium comprising instructions for causing one or more processors to:

identify, in a cardiac signal sensed by a medical device via one or more electrodes, a set of premature ventricular contractions (PVCs) of a heart of a patient;

determine, for each PVC of the set of PVCs, whether the PVC meets PVC storage criteria, wherein a first one or more PVCs of the set of PVCs meet the PVC storage criteria, and wherein a second one or more PVCs of the set of PVCs do not meet the PVC storage criteria; and store, in a memory and for each PVC of the first one or more PVCs that meet the PVC storage criteria, a portion of the cardiac signal corresponding to each PVC of the first one or more PVCs.

\* \* \* \* \*